US000001298H

United States Statutory Invention Registration [19]

[11] Reg. Number: H1298

[43] Published: Apr. 5, 1994

Ahr et al.

[54] FIBROUS SUPERABSORBENT CORE HAVING INTEGRALLY ATTACHED HYDROPHOBIC FACING LAYER

[76] Inventors: Nicholas A. Ahr; David M. Ooten, both of 6100 Center Hill Rd., Cincinnati, Ohio 45224

[21] Appl. No.: 893,963

[22] Filed: Jun. 4, 1992

Related U.S. Application Data

[63] Continuation of Ser. No. 608,083, Nov. 1, 1990, abandoned.

[51] Int. Cl.[5] ..... D04H 1/04

[52] U.S. Cl. ..... 428/296

[58] Field of Search ..... 428/192, 280, 282, 284, 428/285, 286, 288, 298, 326, 346

[56] References Cited

U.S. PATENT DOCUMENTS

| | | | |
|---|---|---|---|
| 3,067,747 | 12/1962 | Wolterding et al. | 128/296 |
| 4,047,534 | 9/1977 | Thomaschefsky et al. | 128/461 |
| 4,397,644 | 8/1983 | Matthews et al. | 604/378 |
| 4,844,965 | 7/1989 | Foxman | 428/91 |
| 4,855,179 | 8/1989 | Bourland et al. | 428/280 |
| 4,886,697 | 12/1989 | Perdelwitz, Jr. et al. | 428/192 |
| 4,939,017 | 7/1990 | Foxman | 428/192 |
| 5,015,245 | 5/1991 | Noda | 604/367 |

FOREIGN PATENT DOCUMENTS

| | | | |
|---|---|---|---|
| 0198683 | 10/1986 | European Pat. Off. | A61F 13/18 |
| 0336578 | 10/1989 | European Pat. Off. | A61F 13/16 |

*Primary Examiner*—Robert L. Stoll
*Assistant Examiner*—Joseph D. Anthony

[57] ABSTRACT

Absorbent structures are disclosed comprising a fibrous, superabsorbent core and an integrally attached facing layer.

The structures can be made by forming nonwoven webs of mixtures of thermoplastic fibers and superabsorbent fibers, and a web consisting essentially of thermoplastic hydrophobic fibers. The layers are bonded together using thermal bonding.

The structures are suitable for use in disposable absorbent products, in particular, pantiliners.

6 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

FIBROUS SUPERABSORBENT CORE HAVING INTEGRALLY ATTACHED HYDROPHOBIC FACING LAYER

This is a continuation of application Ser. No. 07/608,083, filed on Nov. 1, 1990, now abandoned.

TECHNICAL FIELD

The present invention relates to absorbent structures comprising a fibrous superabsorbent core and an integrally attached hydrophobic facing layer.

Absorbent articles designed for absorbing body fluids typically comprise a hydrophillic absorbent core and a hydrophobic facing layer. The function of the facing layer is to wick body fluids away from the body into the absorbent core. Because the facing layer itself is hydrophobic, it will stay relatively dry, thus preventing the discomfort of a wet material in contact with the skin of the user of the absorbent article.

It is desirable to provide a good contact between the hydrophobic facing layer and the hydrophillic absorbent core, so as to enhance fluid transport from the facing layer to the core. It is further desirable to provide an absorbent core having a low bulk, yet a high absorbent capacity. It is further desirable that the absorbent core exhibits good wicking of fluid in the x- and y-directions.

It is therefore an object of the present invention to provide a fibrous superabsorbent core with an integrally attached hydrophobic facing layer. It is a further object of this invention to provide such a core having low bulk and yet a high absorbent capacity.

BACKGROUND ART

U.S. Pat. No. 3,067,747, issued Dec. 11, 1962 to Wolterding et al. discloses absorbent nonadherent bandages for surgical or menstrual use. The bandages have topsheets of nonwoven web of bonded synthetic hydrophobic fibers. The absorbent web may be a combination of cotton and/or rayon fibers mixed with thermoplastic fibers. The topsheet is thermally bonded to the absorbent web.

U.S. Pat. No. 4,047,534, issued Sep. 13, 1977 to Thomaschefsky et al. relates to nursing pads having an inner absorbent layer including a proportion of synthetic thermoplastic polymer fibers and an outer layer of thermoplastic polymer fibers. The layers are combined by embossing with heat and low pressure.

U.S. Pat. No. 4,397,644, issued Aug. 9, 1983 to Matthews et al. discloses a topsheet for sanitary napkins, having a hydrophilicity gradient. The topsheet consists of two layers. The top layer is thermoplastic, for example, spun bonded polypropylene. The so called transfer layer contains from 40 to 100 percent thermoplastic fibers.

U.S. Pat. No. 4,844,965, issued Jul. 4, 1989 to Foxman, relates to an absorptive device for incontinent patients. The device includes a liquid permeable absorptive member having an outer facing layer of synthetic fabric and an inner backing layer of fabric having a blend of thermal plastic and cellulose fibers. The synthetic outer facing layer is ultrasonically welded to the thermal plastic fibers of the blended material inner backing layer.

U.S. Pat. No. 4,844,965, issued Jul. 4, 1989 to Foxman, discloses an absorptive member (for example a bed pad) having an outer facing layer of thermal plastic material and an inner facing layer which has a material blend of thermal plastic and cellulose fibers. This synthetic outer facing layer is ultrasonically welded to the thermal plastic fibers of the blended material inner backing layer. The pad is washable.

U.S. Pat. No. 4,886,697, issued Dec. 12, 1989 to Perdelwitz, Jr. et al. relates to materials having at least one layer comprising a mixture of thermoplastic and other fibers which may be covered with thermoplastic material containing cover sheets. The materials are densified in discrete areas, and eventually cut within the densified region. The layer comprising a mixture of thermoplastic and other fibers may additionally contain a superabsorbent material. The facing layer may be thermobonded to the absorbent layer by pulling heated air through the web plus facing layer. The material is disclosed to be suitable for use in children's car seats.

U.S. Pat. No. 4,939,017, issued Jul. 3, 1990 to Foxman discloses an absorbent pad having an outer layer of 100 percent synthetic thermal plastic fabric and an absorptive layer which is a blend of plastic and cellulose fibers. The layers are ultrasonically welded.

DETAILED DESCRIPTION OF THE INVENTION

The absorbent structures of the present invention comprise a fibrous superabsorbent core with an integrally attached hydrophobic facing layer. Specifically, the absorbent core comprises from about 5 percent to about 95 percent of superabsorbent fibers, and from about 5 percent to about 95 percent of a synthetic thermoplastic fibers. The hydrophobic facing layer consists essentially of synthetic hydrophobic thermoplastic fibers. The structure may be formed on a conventional carding machine, using one card for the hydrophobic facing layer, and one or more cards (up to about 20) for the absorbent core. The layers are integrally bonded by a thermal process. Preferably the bonding is carried out with heated calender rolls or using ultrasonic sealing. This has the additional advantage that during the bonding the bulk of the absorbent structure may be significantly reduced. For example, the caliper of the absorbent structures may be reduced by a factor of 5 to 15 during the thermobonding process. Preferably, the bonding pattern is discontinuous, as is the case when heated embossing rolls are used. In areas where the fibers are not bonded they remain soft and flexible. Moreover, in unbonded areas the superabsorbent fibers absorb fluid and swell more freely than in bonded areas.

The synthetic hydrophobic fibers of the facing layer may be any of such fibers known in the art for this type of application. Polyolefin fibers are preferred, with polypropylene fibers being highly preferred.

The thermoplastic fiber component of the absorbent core may be a hydrophilic or a hydrophobic fiber. If a hydrophobic fiber is used it may be the same or different than the hydrophobic fiber of the facing layer.

Any superabsorbent fiber known in the art may be used as a superabsorbent fiber in the absorbent core. Superabsorbent fibers may be formed by forming a water soluble superabsorbent polymer into water soluble filaments, contacting the filaments with a primary air stream having a velocity effective to attenuate and to partially dry the filaments, and contacting the attenuated filaments with a secondary air stream having a velocity effective to fragment the filaments into fibers. Particularly suitable superabsorbent polymers are polymers comprising a blend of (1) a copolymer of at least one alpha, beta-unsaturated carboxylic monomer and at least one monomer copolymerizable therewith, and (2) a cross-linking agent having crosslinking functionality comprising hydroxyl or heterocyclic carbonate groups. Highly preferred are maleic anhydride/isobutylene copolymers crosslinked with propylene carbonate or a mixture of pentaerythriol and butanediol.

Particularly preferred for use herein is Fibersorb, a commercially available superabsorbent fiber from Arco Chemical Company of Newton Square, Pa. These fibers are disclosed more fully in U.S. Pat. No. 4,855,179, issued Aug. 8, 1989, to Bourland et al., the disclosures of which are incorporated herein by reference. In addition to the hydrophobic fibers and the superabsorbent fibers, the absorbent core may further comprise additional absorbent fibers, like pulp fibers, cotton fibers or rayon. Preferred absorbent cores comprise from about 30 to about 70 percent hydrophobic fibers and from about 70 percent to about 30 percent superabsorbent fibers.

It is advantageous to use calender rolls having an embossing pattern for the thermobonding of the two layers. An example of a suitable embossing pattern is one having a wafer-like or diamond shape pattern of the type disclosed in U.S. Pat. No. 4,781,710, issued Nov. 1, 1988 to Megisan et al., the disclosures of which are incorporated herein by reference.

The absorbent structures of the present invention can be made very thin, i.e., having a thickness of less than about 2 millimeters, preferably less than about 1 millimeter, typically from about 0.3 to about 2 millimeters. Yet, the absorbent structures may have an absorbent capacity of more than 0.05 grams of a 0.9 percent saline solution per square centimeter of the absorbent structure. Typically, the absorbent capacity is in the range of from about 0.07 grams per square centimeter to about 0.25 grams per square centimeter for a structure having a thickness of 1 millimeter.

Preferred absorbent structures have a density in the range from about 0.08 grams per cubic centimeter to about 0.25 grams per cubic centimeter.

The absorbent structures of the present invention are particularly suitable for use in so called pantiliners. Pantiliners are absorbent pads used for the absorption of menstrual fluid during those days of the menstrual cycle that the discharge of menstrual fluid is low. Pantiliners are also commonly used for the absorption of vaginal discharge other than menses.

A pantiliner of the state of the art typically comprises a hydrophobic liquid pervious topsheet, a thin absorbent core, typically comprised of wood pulp fibers, and a liquid impervious backsheet, commonly a polyethylene film. The outer surface of the liquid impermeable backsheet may be provided with strips or blots of a pressure sensitive adhesive for fastening pantiliner in the crotch of the panties of the wearer. Commonly this pressure sensitive adhesive is protected from contamination and inadvertent adherence with a release liner. The release liner is to be removed by the user prior to adhering pantiliner to the panty. Pantiliners may have a length in the range of from 12 centimeters to about 16 centimeters, and a width of from about 3 centimeters to about 8 centimeters. A particularly desirable pantiliner has a slight dog bone shape, a length of about 14 centimeters, a narrowest width in its center portion of about 4 centimeters, and a greatest width near both ends of about 7 centimeters.

Examples of prior art pantiliners are disclosed in U.S. Pat. No. 4,738,676, issued Apr. 19, 1988 to Osborn III, the disclosures of which are incorporated herein by reference.

The absorbent structures of the present invention replace the hydrophobic topsheet and the absorbent core of a conventional pantiliner. It is desirable to provide the absorbent structure with a liquid impervious backsheet. This backsheet may be a suitable film of polyethylene or polypropylene. The backsheet can be thermally bonded or adhesively bonded to the absorbent structure. For adhesive bonding, a preferred adhesive pattern is a spiral spray or meltblown ("angel hair") pattern.

It is desirable to seal the absorbent structure around its perimeter, to prevent superabsorbent fibers from coming into contact with the skin of the wearer. Thermal embossing is a suitable method for sealing the perimeter of absorbent structures of the present invention.

DETAILED DESCRIPTION OF A PREFERRED EMBODIMENT

The following three nonwoven webs are prepared on a nonwoven carding line. A polypropylene web having a basis weight of about 1 ounce per square yard (about 30 grams per square meter) and two nonwoven webs of a 50/50 blend of polypropylene fibers and Fibersorb superabsorbent fiber, each having a basis weight of about 1 ounce per square yard (about 30 grams per square meter). The three webs are combined, such that the all polypropylene layer is the top layer. The combined webs have a thickness of about ½ inch (about 12 millimeters). The combined webs are then calendered at a web speed of about 25 to 30 feet per minute (about 7.5 to 9 meters per minute) and at a temperature of from 140° C. to about 165° C., preferably from about 150° C. to about 160° C. The temperature should be increased when working at higher web speeds, and decreased when working at lower web speeds, to maintain good results. The calender pressure is about 160 pounds per linear inch (about 29 kilogram per linear centimeter). The calender rolls have an embossing pattern of a diamond shape, of the type described in U.S. Pat. No. 4,781,710. The resulting absorbent structure has a caliper of about 0.8 millimeters. It has an absorbent capacity for a 0.9 percent saline solution of about 0.12 grams per square centimeter. Properly dimensioned strips of the absorbent structure are combined with a polyethylene backsheet material and provided with a panty fastening adhesive in the manner described hereinabove for conventional pantiliners. The resulting pantiliner is thin and flexible, yet has adequate absorbent capacity.

In an alternate embodiment the liquid impermeable backsheet is formed as follows. Prior to calendering the nonwoven webs described hereinabove are combined with an additional web consisting essentially of heat fusible fibers, for example, polyethylene fibers. This bottom layer is subsequently rendered liquid impermeable by heat fusing the fibers, for example, using a heated calender roll or infrared radiation.

Similar structures are formed using 1 layer of polypropylene fibers and 3 layers of an 85/15 mixture of polypropylene/Fibersorb fibers.

What is claimed is:

1. A disposable absorbent pad for the absorption of vaginal discharges comprising a fibrous superabsorbent core, an integrally attached hydrophobic facing layer and an integrally attached impervious backsheet, wherein the hydrophobic facing layer consists of essentially synthetic hydrophobic thermoplastic fibers, the absorbent core comprises from about 5% to about 95% of superabsorbent fibers and from about 5% to about 95% of synthetic thermoplastic fibers, and the impervious backsheet is formed by heat fusing a web consisting essentially of heat fusible fibers.

2. An absorbent pad according to claim 1 having a thickness of from about 0.3 mm to about 2 mm and an absorbent capacity for a 0.9% saline solution of from about 0.05 g to about 0.25 g per $cm^2$ of absorbent pad.

3. An absorbent pad according to claim 1 wherein the synthetic hydrophobic thermoplastic fiber is a polyolefin fiber.

4. An absorbent pad according to claim 1 wherein the superabsorbent fibers comprise a copolymer of maleic anhydride and isobutylene.

5. An absorbent pad according to claim 1 wherein the absorbent core comprises from about 30% to about 70% of superabsorbent fiber and from about 30% to about 70% of synthetic thermoplastic fiber.

6. An absorbent pad according to claim 1 wherein the heat fusible fiber is a polyethylene fiber.

* * * * *